United States Patent [19]

Wagner

[11] Patent Number: 4,861,728
[45] Date of Patent: Aug. 29, 1989

[54] IMMUNOASSAY OF GLYCOSYLATED HEMOGLOBIN USING A LABELED BORON REAGENT

[75] Inventor: Daniel B. Wagner, Raleigh, N.C.

[73] Assignee: Becton, Dickinson and Company, Franklin Lakes, N.J.

[21] Appl. No.: 77,363

[22] Filed: Jul. 24, 1987

[51] Int. Cl.$^4$ .................. G01N 33/566; G01N 33/72
[52] U.S. Cl. .................................... 436/501; 436/522; 436/525; 436/527; 436/529; 436/530; 436/531; 436/66; 436/67; 436/800; 436/815
[58] Field of Search ............... 436/66, 67, 501, 522, 436/525, 527, 529, 530, 531, 800, 815

[56] References Cited

U.S. PATENT DOCUMENTS

| | | |
|---|---|---|
| 4,222,836 | 9/1980 | Kerr et al. |
| 4,269,605 | 5/1981 | Dean et al. ............ 436/67 |
| 4,270,921 | 6/1981 | Graas . |
| 4,351,711 | 9/1982 | Ambler . |
| 4,371,374 | 2/1983 | Cerami et al. ......... 436/87 |
| 4,389,491 | 6/1983 | Hanamoto et al. |
| 4,407,961 | 10/1983 | Sanders . |
| 4,409,335 | 10/1983 | Hanamoto et al. |
| 4,436,820 | 3/1984 | Reiter . |
| 4,658,022 | 4/1987 | Knowles et al. ....... 436/819 X |
| 4,777,128 | 10/1988 | Lippa . |

OTHER PUBLICATIONS

Yoshitake et al., Conjugation of Glucose Oxidase from Aspergillus niger and Rabbit Antibodies Using N-Hydroxysuccinimide Ester of N-(4-Carboxycyclohexylmethyl)-Maleimide, Eur. J. Biochem. 101, 395–9 (1979).

Carlsson et al., Protein Thiolation and Reversible Protein-Protein Conjugation, Biochem. J. 173, 723–737 (1978).

Primary Examiner—Esther M. Kepplinger
Assistant Examiner—Richard Wagner
Attorney, Agent, or Firm—Richard E. Brown

[57] ABSTRACT

A method for determining the percentage of glycosylated hemoglobin in the total hemoglobin of a blood sample includes binding of both glycosylated and nonglycosylated hemoglobin competitively to a nonspecific binder for hemoglobin afixed to a dipstick and reacting the glycosylated hemoglobin with a dihydroxyboryl reagent conjugated to a fluorescent dye. When the binding and reacting steps are complete, the dipstick is washed and its color is measured by absorption of incident light having a wavelength within the absorption range of hemoglobin as an indication of total hemoglobin in the sample. Incident light having a wavelength within the absorption range of the dye is then applied to the dipstick and fluorescence from the dipstick is measured as an indication of glycosylated hemoglobin. The measurements may be made with a reflectometer capable of computing the percentage of glycosylated hemoglobin in the sample from the color and fluorescence measurements. The invention includes a kit of materials useful for performing the assay method of the invention.

16 Claims, 4 Drawing Sheets

4,861,728

IMMUNOASSAY OF GLYCOSYLATED HEMOGLOBIN USING A LABELED BORON REAGENT

BACKGROUND OF THE INVENTION

1. Field of the Invention. This invention relates to a method for assay of glycosylated hemoglobin, and more particularly, to a homogeneous method and materials for determination of the percentage of glycosylated hemoglobin in the total hemoglobin of a blood sample.

2. Background of the Invention. Hemoglobin (Hb) is a mixture of proteins consisting of a prosthetic heme group attached to two pairs of unlike polypeptide chains, and, in this disclosure, Hb refers in general to this mixture. In the major component of the mixture, conventionally termed HbA, the chains are designated $\alpha$ and $\beta$. Total Hb, hereinafter termed Hbt, includes the major $\alpha_2$, $\beta_2$ fraction and several minor components having different chains, and various hemoglobin fractions formed by nonenzymatic glycosylation reactions of intact Hb molecules. As used in this disclosure, Hb and Hbt actually designate the same material. For clarity, Hbt is used to emphasize total hemoglobin, and Hb is used for general discussion which can apply to any hemoglobin fraction or combination of fractions.

The fractions of Hb are conventionally separated by chromatography. The main chromatographic fraction, making up about 90% of Hbt, is nonglycosylated and is generally referred to as HbA, and, in this disclosure, the term HbA is used to designate total nonglycosylated Hb. The major fraction of glycosylated Hb, conventionally and in this disclosure, is termed HbAlc.

HbAlc arises by reaction of a terminal valine amino group in the $\beta$ chain with the aldehyde group of glucose to give an unstable aldimine. Amadori rearrangement of the aldimine gives HbAlc, which is characterized by a $\beta$-ketoglycoside linked to the valine amine group.

The determination of HbAlc and the percentage thereof in Hbt is important in the diagnosis of diabetes mellitus and in monitoring the treatment of diabetic patients. In nondiabetic people, the HbAlc level is generally between 4–8% of Hbt. In diabetics, the HbAlc level is 2-3 fold higher and may range up to 20% of Hbt.

A variety of methods has been proposed for assessment of HbAlc and Hbt levels in a sample of a patient's blood. Early macrochromatographic separation methods have been supplanted by microchromatography methods using ion-exchange resins as column packing. U.S. Pat. Nos. 4,270,921 to Graas, 4,389,491 to Hanamoto, 4,436,820 to Reiter and 4,407,961 to Sanders are exemplary of HbAlc determinations using ion-exchange techniques. Hanamoto, in U.S. Pat. No. 4,409,335 uses a dihydroxyboryl complex of HbAlc in an ion-exchange method.

Other disclosures achieve separation without ion-exchange. Electrophoretic separation is described in U.S. Pat. No. 4,351,711 to Ambler. Electrochromatographic separation is disclosed in U.S. Pat. No. 4,222,836 to Kerr.

U.S. Pat. No. 4,269,605 to Dean discloses separation of a dihydroxyboryl complex of HbAlc from other Hb fractions by physical means, such as by bonding the boryl reagent to a solid phase, so that HbA can be washed away.

All existing methods for determination of HbAlc involve separation of the HbAlc from Hbt prior to measurement. These separation steps entail repeated accurate pipetting steps and are costly, time-consuming, labor intensive procedures requiring skilled technicians. There is a definite need for a simple, rapid, accurate assay which can be performed by unskilled technicians. It is toward the fulfillment of this need that this invention is directed.

SUMMARY OF THE INVENTION

A method for determining the percentage of HbAlc in a blood sample relative to the Hbt of the sample is based on reaction of the glycoside portion of HbAlc with a reagent which does not react with HbA. The reagent is conjugated to a fluorescent dye and combined with a lysed blood sample to give a mixture. The mixture is contacted with a solid phase consisting of a solid support having affixed thereto a binder for Hb. Conditions are provided to cause HbA and HbAlc to bind to the binder and to cause reaction between the reagent and the HbAlc. The solid phase is separated from the mixture, and the color of the solid phase is read to provide a measure of Hbt. Incident light of a wavelength within the absorption range of the dye is applied to the solid phase and fluorescence from the dye provides a measure of HbAlc. From the measured color and fluorescence, the percentage of HbAlc in the Hbt of the sample may be computed.

A referred binder is an antibody specific for Hb (hereinafter referred to as anti Hb) coated onto the solid phase. The most preferred solid phase is a dipstick having the antibody covalently conjugated thereto.

The preferred reagent is a dihydroxyboryl compound which may be covalently conjugated to the fluorescent dye. The most preferred reagent is m-aminophenylboronic acid which may be conjugated to the dye by means of the amino group. The most preferred dye is phycoerythrin.

Color is preferably measured with a reflectometer which, with the addition of an appropriate filter, may also be used to measure fluorescence.

Another aspect of the invention is a kit of materials useful in performing the method of the invention.

Thus, in accordance with the invention, a method and materials useful for determining HbAlc preferably takes advantage of the reaction of the glycoside portion of HbAlc with a dihydroxyboryl reagent. The method may be performed with a simple dipstick solid phase which avoids tedious separation steps of conventional column based methods yet allows HbAlc to be determined in the presence of HbA. Because delicate assay operations, such as critical volume measurements and pipetting steps, are avoided, the assay may be performed by unskilled technicians and, because simple, conventional and inexpensive equipment is used, may be performed in physician's offices or even in the home.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention of the embodiments illustrated and described. The scope of the invention will be measured by the appended claims and their equivalents.

The present invention is directed to a method for determining the percentage of HbAlc in the Hbt of a blood sample which may be performed without prior separation of the HbAlc and the Hbt. The method includes reaction of the glycoside portion of HbAlc with a reagent which does not react with HbA. The chemistry upon which the present invention is based is illustrated with the aid of the figures. In the figures, HM means heme, a colon represents a binding and an asterisk represents a covalently bound fluorescent dye.

Figure 1:
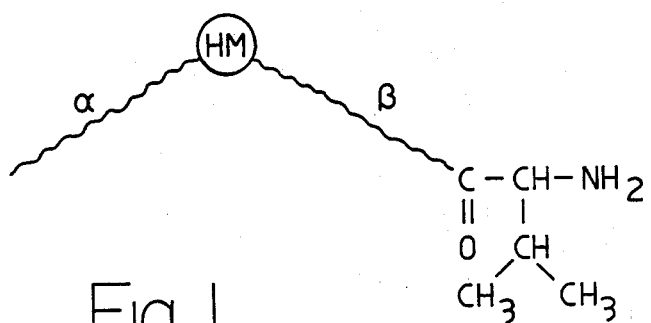
FIG. 1 is a partial structural schematic of an HbA molecule.
Figure 2:
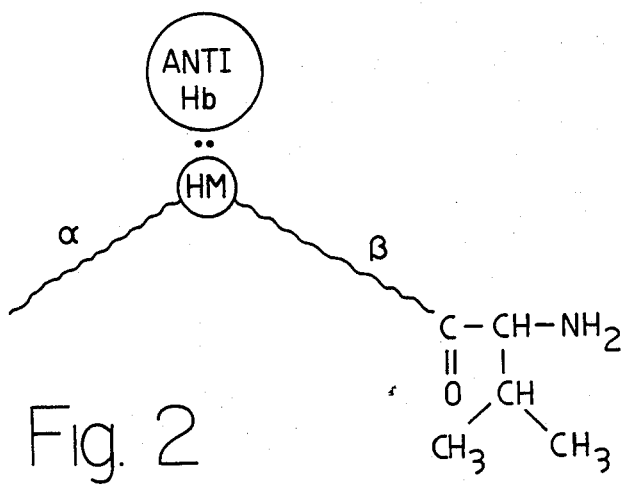
FIG. 2 is a partial structural schematic of a complex of the HbA molecule of FIG. 1 and an antibody.

FIG. 1 shows in schematic form an HbA molecule having a heme prosthetic group and an α chain and a β chain terminating in the amino group of a valine residue. It is generally believed that when Hb binds to a nonspecific binder, as, for example, anti Hb, binding takes place through the heme group. FIG. 2 shows the HbA molecule of FIG. 1 bound to anti Hb at the site of the heme component.

Figure 3:
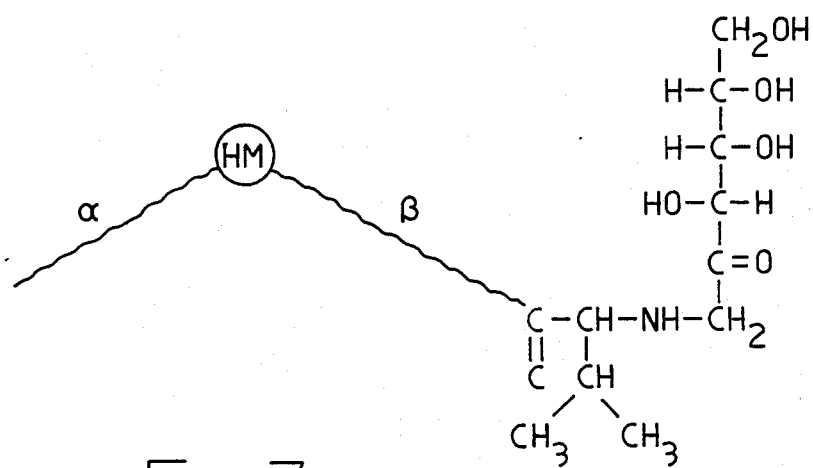
FIG. 3 is a partial structural schematic of an HbAlc molecule.
Figure 4:
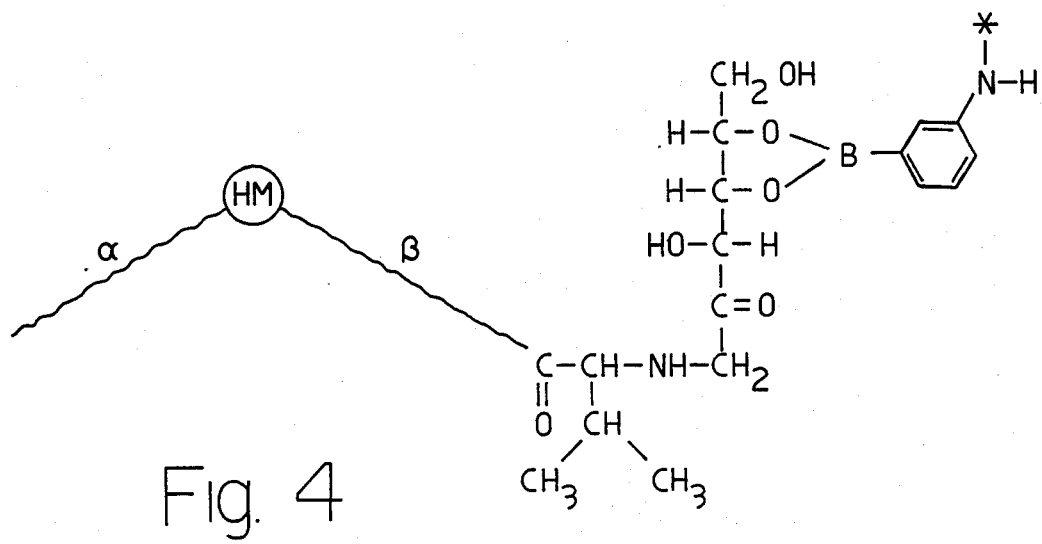
FIG. 4 is a partial structural schematic of a complex of the HbAlc molecule of FIG. 3 and a labeled dihydroxyboryl reagent.
Figure 5:
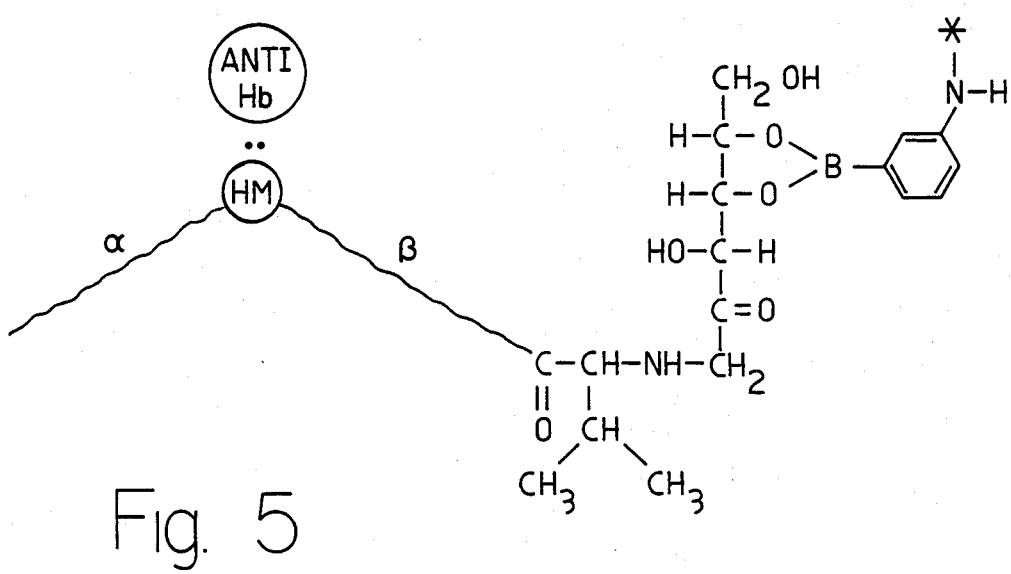
FIG. 5 is a partial structural schematic of the complex of FIG. 4 with an antibody.

FIG. 3 shows the polyhydroxy β-ketoglycoside structure of HbAlc resulting from reaction of the valine amine group with glucose and Amadori rearrangement of the intermediate aldimine (not shown). Polyhydroxy compounds are known to react with various reagents to form complexes. FIG. 4 shows a complex of HbAlc with the preferred dihydroxyboryl reagent of the invention wherein the asterisk represents a fluorescent dye. It is seen that the heme group of the complex remains free and available to bind to anti Hb, as illustrated in FIG. 5.

The assay of the invention includes a solid phase and a fluid phase. The solid phase consists of a nonspecific binder for Hb affixed to a solid support. The preferred binder is anti Hb which is affixed to the support in limited quantity so that the HbA and the labeled HbAlc bind to and occupy substantially all of the anti Hb. This binding is competitive so that the HbA and HbAlc bind to the anti Hb in proportion to their concentrations in the blood sample.

As known in the art, the solid support may be any support which does not interfere with the assay. Exemplary of, but not limited to, solid supports which may be used are glass and polymeric materials, such as polyethylene, polystyrene, polymethylmethacrylate, polyacrylamide and the like. Such supports may be fabricated into any suitable shape, such as sheets, plates, wells, tubes or, preferably, dipsticks.

In a preferred embodiment of the invention, the nonspecific binder is anti Hb coated onto the surface of a polystyrene dipstick. The coating of anti Hb may be applied by any conventional technique, such as physical absorption or, preferably, covalent conjugation.

Subsequently to preparing the anti Hb coated dipstick, any remaining binding sites on the dipstick are filled with an inert protein, such as albumin. Methods to attach binding molecules, such as antibodies and albumin to a solid support are well-known in the art and further details in this respect are not needed for a complete understanding of the invention.

The fluid phase of the assay consists of a mixture of a liquid assay vehicle and a dye-labeled reagent to which is added a blood sample containing an unknown percentage of HbAlc. The order in which these assay components are combined is not critical.

Any vehicle may be used which does not interfere with the binding reactions and signal measurements described below. Suitable vehicles are for example, water, saline buffers and, preferably, phosphate buffered saline (PBS).

The reagent of the invention may be any substance which can be conjugated to a fluorescent dye and which reacts with HbAlc but not with HbA or any other material in the fluid phase. In this way, the only labeled material in the fluid phase other than the dye labeled reagent itself is the labeled HbAlc.

Suitable reagents are boron derivatives such as boric acids or, preferably, boronic acids. The most preferred reagents are arylboronic acids having a functional group to which the fluorescent dye may be covalently conjugated. Exemplary of such reagents is m-aminophenylboronic acid.

Any fluorescent dye may be used which has an absorption maximum in a region of the spectrum different from that of Hb. Preferred dyes have an absorption range above about 450 nm and a Stokes shift greater than 30 nm, most preferably about 50 nm. Exemplary of suitable dyes are fluorescein, rhodamine and phycobiliprotein. The most preferred dyes are phycobiliproteins such as phycoerythrin.

Conjugation of the dye to the dihydroxyboryl reagent is conventional and fully understood by those in the art. For example, a fluorescinated reagent may readily be prepared by reaction of m-aminophenylboronic acid with fluorescein isothiocyanate (FITC).

A blood sample containing an unknown quantity of HbAlc to be determined as a percentage of the Hbt in the sample may be added directly to the fluid phase of the assay mixture. It is understood that the erythrocytes of the sample should undergo lysis to release the Hbt therefrom before complexation of the HbAlc with the reagent can occur. Lysis may be induced merely by allowing the mixture of the blood sample and the assay vehicle to remain in contact for a suitable time. Preferably, an exogenous lysing agent may be added. Any lysing agent standard in the art may be used, as, for example, the polyoxyethylenesorbitan ester detergents.

Alternatively, the erythrocytes may be lysed prior to being combined with the reagent in the assay vehicle. If desired, the lysate may be centrifuged, the pellet discarded and only the supernatant combined with the assay vehicle.

Reaction of HbAlc with the labeled reagent in the fluid phase occurs readily upon contact and provides HbAlc in labeled form. It is generally sufficient merely to maintain contact at ambient temperature for a few minutes. If desired, the fluid phase may be incubated at from 25° to 35° C. for 10 to 30 minutes to enhance the reaction.

The solid and liquid phases may be brought into contact to induce binding between the anti Hb on the solid support and the HbA and labeled HbAlc in the fluid phase. The method for bringing the two phases into contact of course depends on the nature of the solid phase. When the solid phase is the preferred dipstick, mere submersion of the dipstick into the fluid phase for a suitable time is sufficient. Binding may, if desired, be facilitated by an incubation step carried out at from 25° to 35° C. for 10 to 30 minutes.

When binding is complete, the dipstick is removed from the fluid phase, washed thoroughly, generally until the washings no longer contain any Hb, and both its color and fluorescence are measured. Since all Hb fractions are the same color, the color of the dipstick provides a measure of Hbt. On the other hand, the only Hb fraction on the dipstick which fluoresces is the HbAlc bound to the dye-labeled reagent. Measurement of fluorescence thus provides a measure of HbAlc.

Any method for measuring these two parameters may be used. A preferred method is reflectometry. In this technique, incident light strikes the dipstick at an angle and is reflected therefrom rather than being transmitted therethrough, as in conventional colorimetry. However, since the dipstick is coated with a layer containing HbA and dye-labeled HbAlc, some of the incident light, if it is of a proper wavelength, will be absorbed by these Hb fractions so that the difference between the intensity of the incident light and the intensity of the reflected light is proportional to the Hbt in the sample. Any incident light of a wavelength whereby it is absorbed by Hb may be used for determination of Hbt in accordance with the method of the invention. Preferably, the incident light includes light having a wavelength around 416 nm since all Hb fractions absorb strongly in this wavelength region.

The reflectometer may be equipped with filters so that the wavelength of the incident light can be adjusted by simple manipulations. When the dipstick is subjected to incident light having a wavelength within the absorption range of the fluorescent dye portion of the labeled HbAlc, a portion of the light proportional to the concentration of HbAlc in the sample will be absorbed by the dye and reflected therefrom as fluorescence emission. The intensity of the fluorescence thus provides a measure of the HbAlc in the sample. The instrument may preferably be provided with computing capability whereby the ratio of HbAlc in the Hbt of the sample is calculated directly from the absorption due to the Hbt and the fluorescence due to the HbAlc, and the results are then provided in digital read-out form.

As mentioned above, all Hb fractions are the same color, and substantially all of the anti Hb binding sites on the dipstick are saturated with bound HbA or HbAlc. Accordingly, in another embodiment of the invention, the color of the dipstick at the conclusion of the assay procedure may be considered to be constant so that measurement of the absorption at about 416 nm may be eliminated. For this embodiment of the invention, the reflectometer may be adapted to compute the percentage of HbAlc directly from the fluorescence reading alone.

Another aspect of the invention is a kit of materials useful in performing the method of the invention. The kit may include a solid phase having affixed thereto a nonspecific binder for Hb and a fluorescent dye-labeled dihydroxyboryl reagent, preferably supplied in solid form in a container adapted to serve as the assay reaction vessel.

The kit may also include a blood lysing agent and solutions containing known concentrations of Hb and HbAlc, alone or combined, and a solution devoid of Hb and HbAlc to serve as a negative control. Other solutions and utensils such as saline, buffers, diluents, vials, droppers and the like useful in performing the assay may also be provided.

The following example is provided to further describe the invention.

EXAMPLE I (a) Conjugation of m-aminophenyl Boronic Acid with R-Phycoerythrin

R-Phycoerythrin is converted to a pyridyldisulfide derivative with N-succinimidyl-3-(2-pyridyldithio)propionate according to the published procedure [*Biochemical J.* 173:723 (1978)] and then reduced to a thiol with dithiothreitol. Using standard procedure, a maleimide derivative of m-aminophenyl boronic acid is reacted with the derivatized R-phycoerythrin using succinimidyl-4-(N-maleimidomethyl)-cyclohexane-1-carboxylate (SMCC) [*Eur. J. Biochem.* 101:395 (1979)] to obtain phycoerythrin conjugated boronic acid.

(b) Coupling of Anti-human Hemoglobin Antibody on Solid Surface

Using procedures already known in the art, polystyrene sheets are incubated in appropriate buffer solutions containing anti-human hemoglobin antibody. After optimum binding is achieved, the sheets are further incubated in solutions containing bovine serum albumin according to known procedure. The anti-human hemoglobin bonded polystyrene sheets so obtained are used for test purposes.

(c) Preparation of Assay Solution

An assay solution is prepared by mixing the phycoerythrin conjugated boronic acid and the surfactant supplied in the kit in a proper buffer solution.

(d) Assay of Glycosylated Hemoglobin in a Patient's Blood

A drop of the patient's blood is added to the assay solution and gently shaken to allow for blood lysing and conjugation of the glycosylated hemoglobin with the dye-labeled boronic acid. To this medium is then dipped the polystyrene sheet dipstick containing immobilized anti-human hemoglobin. After complete binding of hemoglobin on the available antibody binding sites, the dipstick is withdrawn, washed in a suitable buffer, pressed between absorbent papers, and inserted inside a reader which has been previously standardized. The reader provides the percentage of glycosylated hemoglobin in the sample based on a standard curve previously prepared with blood samples containing known quantities of glycosylated hemoglobin.

Thus, in accordance with the invention, a simple dipstick or like method is provided to determine the percentage of HbAlc in the Hbt of a blood sample. The method uses the known complexation of HbAlc with a dihydroxyboryl reagent, but avoids the conventional column-based separation of HbAlc from HbA. The method thus achieves its objective in significantly less time without requiring any accurate measurements of assay reagents. The method does not even require an accurate measure of the blood sample; in general, a technician need only add a drop of blood to the assay components. Since the instrument is simple in design, inexpensive and may provide the desired result in simple digital readout form, there is no need for trained technicians. The method is thus ideally adapted to HbAlc determinations in clinics, physician's offices and even in the home.

What is claimed is:

1. A method for determining the percentage of glycosylated hemoglobin in the total hemoglobin of a blood sample comprising:
   (a) contacting a solid support having affixed thereto antibodies that bind to total hemoglobin with a mixture including a blood sample, a lysing agent and a fluorescent dye conjugated to a dihydroxyboryl reagent reactive with glycosylated hemoglobin, whereby hemoglobin and glycosylated hemoglobin in said sample bind to said antibodies and said glycosylated hemoglobin reacts with said reagent;
   (b) separating said support from said mixture;
   (c) applying incident light having a wavelength within the absorption range of hemoglobin and measuring the color of said support;
   (d) applying excitation light having a wavelength within the absorption range of said dye on said support and measuring fluorescence therefrom said excitation wavelength being different from the wavelength of said incident light; and
   (e) determining the percentage of glycosylated hemoglobin in said sample from the intensity of said color and said fluorescence.

2. The method in accordance with claim 1 wherein said solid support is a dipstick.

3. The method in accordance with claim 1 wherein said lysing agent is a polyoxyethylenesorbitan.

4. The method in accordance with claim 1 wherein said dye is selected from the group consisting of fluorescein, rhodamine and phycobiliprotein.

5. The method in accordance with claim 1 wherein said reagent is selected from the group consisting of a boric acid and a boronic acid.

6. The method in accordance with claim 5 wherein said reagent is an aminoarylboronic acid.

7. The method in accordance with claim 1 wherein said measuring steps are performed by reflectometry.

8. The method in accordance with claim 1 wherein said determining is performed by reflectometer.

9. A method for determining the percentage of glycosylated hemoglobin in the total hemoglobin of a blood sample comprising:
   (a) contacting a solid support having affixed thereto antibodies that bind to total hemoglobin with a mixture including a blood sample, a lysing agent and a reagent consisting of phycoerythrin conjugated to m-aminophenylboronic acid whereby hemoglobin and glycosylated hemoglobin in said sample bind to said antibodies and said glycosylated hemoglobin reacts with said reagent;
   (b) separating said support from said mixture;
   (c) applying incident light having a wavelength of about 416 nm to said support and measuring the color of said support;
   (d) applying excitation light having a wavelength within the absorption range of said phycoerythrin to said support and measuring fluorescence from said solid phase said excitation wavelength being different from about 416 nm; and
   (e) determining the percentage of glycosylated hemoglobin in said sample from the intensity of said color and said fluorescence.

10. A kit of materials for determining the percentage of glycosylated hemoglobin in the total hemoglobin of a blood sample comprising a dihydroxyboryl reagent conjugated to a fluorescent dye and a solid support having affixed thereto an antibody for hemoglobin.

11. The kit in accordance with claim 10 further comprising a lysing agent.

12. The kit in accordance with claim 10 further comprising a container to serve as the assay reaction vessel.

13. The kit in accordance with claim 10 further comprising a solution selected from the group consisting of a solution of glycosylated hemoglobin of known concentration, a solution of hemoglobin of known concentration, and a solution containing a known concentration of both hemoglobin and glycosylated hemoglobin.

14. The kit in accordance with claim 10 further comprising a reagent useful in performing the assay method of the invention selected from the group consisting of saline, buffer and diluent.

15. The kit in accordance with claim 10 wherein said support is a dipstick.

16. A kit of materials for determining the percentage of glycosylated hemoglobin in the total hemoglobin of a blood sample comprising a dipstick having affixed thereto an antihemoglobin antibody, and meta aminophenylboronic acid conjugated to a fluorescent dye.

* * * * *